United States Patent [19]

Beyeler et al.

[11] Patent Number: 4,964,929

[45] Date of Patent: Oct. 23, 1990

[54] PREPARATION OF EXPLOSIVES CONTAINING DEGRADATION PRODUCTS OF ASCORBIC OR ISOASCORBIC ACID

[75] Inventors: Paul Beyeler, Arlesheim; Claude Fürbringer, Riehen, both of Switzerland

[73] Assignee: Hoffmann-La Roche Inc., Nutley, N.J.

[21] Appl. No.: 395,379

[22] Filed: Aug. 17, 1989

Related U.S. Application Data

[63] Continuation of Ser. No. 122,102, Nov. 18, 1987, abandoned.

[30] Foreign Application Priority Data

Nov. 27, 1986 [CH] Switzerland ............... 4741/86

[51] Int. Cl.$^5$ .............................. C06B 21/00
[52] U.S. Cl. ......................... 149/109.6; 149/46; 149/60; 149/61
[58] Field of Search ............ 149/46, 60, 61, 109.6

[56] References Cited

U.S. PATENT DOCUMENTS

| | | |
|---|---|---|
| 907,007 | 12/1908 | Ceipek ................... 149/46 |
| 1,056,365 | 3/1913 | Raschig . |
| 1,128,380 | 2/1915 | Sparre .................. 149/61 |
| 2,566,602 | 9/1951 | Simo .................... 149/61 |
| 2,655,694 | 10/1953 | Piper . |
| 3,296,044 | 1/1967 | Gehrig . |
| 3,361,604 | 1/1968 | Griffith . |
| 3,397,637 | 8/1968 | Bobinski et al. . |
| 3,409,708 | 11/1968 | Moore . |
| 3,485,686 | 12/1969 | Jessop et al. . |
| 3,557,700 | 1/1971 | Quinlan et al. . |
| 3,670,649 | 6/1972 | Hartlein et al. . |
| 3,725,516 | 11/1982 | Kaufman . |
| 3,730,094 | 5/1973 | Quinlan . |
| 3,737,350 | 6/1973 | Grant . |
| 3,765,967 | 10/1973 | Funk et al. . |
| 3,783,735 | 1/1974 | Murphy et al. . |
| 3,816,191 | 6/1974 | Wilson et al. . |
| 3,862,866 | 1/1975 | Timmerman et al. . |
| 3,881,993 | 11/1989 | Furbringer et al. ........... 149/109.6 |
| 3,901,153 | 8/1975 | Brabets et al. . |
| 3,908,509 | 9/1975 | Kelly et al. . |
| 3,910,805 | 10/1975 | Catanzarite . |
| 3,919,940 | 11/1975 | Ploger et al. . |
| 3,925,122 | 12/1975 | Berthmann et al. . |
| 3,964,255 | 6/1976 | Catanzarite . |
| 3,971,729 | 7/1976 | Timmerman . |
| 3,987,731 | 10/1976 | Brzuskiewicz . |
| 3,994,235 | 11/1976 | Politzer et al. . |
| 4,025,591 | 5/1977 | Pendergast . |
| 4,051,207 | 9/1977 | Brachert et al. . |
| 4,068,589 | 1/1978 | Oversohl . |
| 4,080,411 | 3/1978 | Stanley . |
| 4,111,727 | 9/1978 | Clay . |
| 4,128,443 | 12/1978 | Pawlak . |
| 4,137,286 | 1/1979 | Bornstein . |
| 4,140,562 | 2/1979 | Gualillo et al. . |
| 4,179,404 | 12/1979 | Barone . |
| 4,335,063 | 6/1982 | Kolb et al. . |
| 4,356,769 | 11/1982 | Galluzzi . |
| 4,394,198 | 7/1983 | Takeuchi et al. . |
| 4,417,465 | 1/1984 | Gonzalez . |
| 4,497,676 | 2/1985 | Kurtz .................... 149/2 |
| 4,728,376 | 3/1988 | Kurtz ................... 149/21 |

FOREIGN PATENT DOCUMENTS 4509 of 1896 United Kingdom .
9111 of 1897 United Kingdom .
796154 6/1958 United Kingdom .

OTHER PUBLICATIONS

*Journal of Agricultural and Food Chemistry*, vol. 17, No. 1, Jan.–Feb., 1969.
Rocket Propellant Handbook, Kit and Evered, The MacMillan Company, pp. 148–151 (1960).

*Primary Examiner*—Edward A. Miller
*Attorney, Agent, or Firm*—George M. Gould; Bernard S. Leon; Alan P. Kass

[57] ABSTRACT

A degradation product of ascorbic acid or isoascorbic acid obtained by heating the acid at a temperature between about 70° C. and about 210° C. until partial or complete decomposition of the acid occurs, useful in admixture with various nitrate-containing oxidation agents as an explosive and propellant material for a wide range of specific applications.

4 Claims, No Drawings

PREPARATION OF EXPLOSIVES CONTAINING DEGRADATION PRODUCTS OF ASCORBIC OR ISOASCORBIC ACID

This is a continuation, of application Ser. No. 07/122,102, filed Nov. 18, 1987, and now abandoned.

DESCRIPTION OF THE INVENTION

The present invention is concerned with a lactone degradation product, namely a degradation product of ascorbic acid or isoascorbic acid, as well as with a process for the manufacture of that degradation product. The present invention is also concerned with the use of the degradation product for the manufacture of explosive materials, such as blasting materials, firing or propellant materials and pyrotechnic materials, and with the explosive materials themselves.

The process of this invention for the manufacture of a degradation product of ascorbic acid or isoascorbic acid comprises heating the acid, preferably in the presence of a substance which promotes the degradation of the acid, to a temperature between about 70° C. and about 210° C., such that about 10-100% of the acid is degraded.

In accordance with a convenient embodiment of the process of the invention, the heating is effected at a temperature between about 80° C. and 190° C., preferably 80° C. to 150° C.

The heating period depends on the heating temperature used and on the equipment employed for the heating. In general, the heating period is relatively short with use of high heating temperatures and relatively longer with use of lower heating temperatures. The heating period can in general be between about one minute and several hours, preferably between about one minute and three hours. Relatively short heating periods, for example, from one minute to about sixty minutes, are possible when microwave ovens or extruders are used.

If desired, the heating can be effected in the absence of air.

The heating of the acid can be conducted in a solid or liquid state, but preferably is carried out in solution, conveniently in aqueous solution, or in suspension, conveniently in aqueous suspension, in order to achieve as uniform as possible a heating of the entire material. Further, it is possible to carry out the heating of the acid in the moist state, preferably in a water-moistened condition. When heating is carried out in solution, or in suspension, or in the moistened condition, the solvent or suspension agent is evaporated during the heating. In such cases, carbon dioxide is also given off.

Alkali salts or alkaline earth salts can be used as substances which promote the degradation of the acid.

According to a preferred embodiment of the process of this invention, an alkali salt or alkaline earth salt of ascorbic acid or isoascorbic acid, especially the sodium or potassium salt, is used as the substance which promotes the degradation of the acid. These salts can also be produced in situ by adding the corresponding hydroxide, carbonate or bicarbonate to the acid.

The salt is conveniently used in an amount of about 0.1 to 100 wt. %, preferably in an amount of 0.5 to 50 wt. %, and most especially in an amount of about 1 to 10 wt. %. The degradation rate is influenced by the amount of ascorbate which is used in the sense that higher amounts of ascorbate lead to a more rapid degradation.

The degradation product of ascorbic acid or isoascorbic acid, which forms a further object of the present invention, is a product obtainable in accordance with the above process, by heating the ascorbic acid or isoascorbic acid, preferably in the presence of a substance which promotes the degradation of the acid, to a temperature between about 70° C. and about 200° C., whereby about 10 to 100% of the acid is degraded.

Such a product, depending on such factors as the heating temperature, heating period, and type and amount of substance used to promote the degradation of the acid, is characterized by the following properties:

A brownish, at least partially water-soluble powder, containing, in addition to non-degraded acid, polymeric substances, furanones and furanols as well as other degradation and transformation products; degree of degradation 10-100 %, for example 40-90% and 60-90%, preferably 65-85%; weight loss compared with starting material 5-40%, especially 10-30%; heat of combustion: 3315 cal/g with a degree of degradation of 50%, 3394 cal/g with a degree of degradation of 65%, and 4200 cal/g and above with higher degrees of degradation.

As mentioned earlier, the degradation product obtained by the process of this invention is suitable for the manufacture of explosive materials. Thus, this degradation product is mixed with a nitrate-containing oxidation agent and, if desired, further additives, for example, gelatinizing agents or stabilizers such as substituted ureas, e.g., Akardit® or Centralit®, substituted urethanes, phthalates, polymers, additives for illuminating compositions such as sodium, barium, strontium or copper salts, as well as other additives, e.g., for increasing the explosive energy or for improving other desirable properties, such as, for example, boron or nitroguanidine.

As the nitrate-containing oxidation agent there is preferably used an alkali or alkaline earth nitrate or ammonium nitrate. Mixtures of such nitrates can also be used.

Other nitrate-containing oxidation agents are organic nitrate esters which are conventionally used as liquid plasticizers for explosive materials and rocket fuels.

The weight ratio of nitrate-containing oxidation agent to degradation product can vary between 90:10 and 50:50, and preferably between 80:20 and 60:40, depending on the intended use of the end product. These ratios relate to potassium nitrate as the nitrate-containing oxidation agent.

For the preparation of an explosive material using the degradation product of this invention and a nitrate-containing oxidation agent, the two substances are mixed with one another, optionally with the addition of other additives. For this purpose it is possible to use dry mixing or to prepare a mixture of the ingredients in a solution, for example an aqueous solution, with subsequent evaporation of this solution to yield a solid residue. The production of a dry end product (the explosive material) by means of spray drying from a solution or suspension has been shown to be especially advantageous. In this connection, by means of methods and equipment known per se such as, for example, an ultrasound vibration nozzle or by suitable temperature control there can be obtained droplets of different sizes and the widest variety of granulates as are suitable for various applications. In addition to spray drying, drying by means of a thin-layer evaporator or a belt dryer is suitable. The manufacture of the end product in the form of granulates via the melt is also possible. It is also possible to carry out the heating of the ascorbic acid or isoascorbic acid in a kneading apparatus and directly admixing therewith the oxidation agent after attaining the specified degree of degradation.

Where desired, a further degradation of the acid can also be carried out during the preparation of the end product (the explosive material) by using a degradation product having a high acid content and continuing the degradation by thermal treatment during the mixing stage or in the formulation of the end product.

An end product obtained in this manner is a material in the form of an explosive, suitable for use in such applications as mining, as a firing or propellant material, as a pyrotechnic material or as an energy-rich mixture which can be utilized for various propulsive purposes.

To illustrate a few specific applications, the end product can be used for the manufacture of shells or cartridges, for illuminating or signal munitions, for rockets, for blasting devices and for fireworks.

The explosive material provided by this invention is characterized by high safety, low corrosivity, high propellant force and low smoke evolution.

DESCRIPTION OF THE SPECIFIC EMBODIMENTS

Example 1

8.95 g of ascorbic acid and 1.05 g of potassium ascorbate are dissolved in 50 ml of $H_2O$ and thereafter evaporated to dryness on a rotary evaporator at 45° C./15 mbar. Subsequently, the dry mixture in a petri dish is left to stand for 3 hours at 130° C. in an oven. In this manner there are obtained 8.5 g of a mixture which still contains about 42% of ascorbic acid.

Example 2

In an analogous experiment to that in Example 1, the mixture is left to stand for 75 minutes at 150° C. Under these conditions there are obtained 7 g of a mixture with an ascorbic acid content of about 7%.

Example 3

895 mg of ascorbic acid and 105 mg of potassium ascorbate are stirred in a glass vessel with 0.4 ml of water and then left to stand for 5 minutes in a microwave oven at 85° C. and 2450 MHz. In this manner there are obtained 990 mg of a mixture which still contains about 85% ascorbic acid.

Example 4

In an analogous experiment to that in Example 3, the mixture is heated for 10 minutes in a microwave oven. This gives about 700 mg of a mixture with a residual ascorbic acid content of about 1%.

Various properties of the degradation product obtained in Examples 1 and 2 are compiled in the following Table:

TABLE

| | Example 1 Ascorbic acid degraded to 42% | | Example 2 Ascorbic acid degraded to 7% |
|---|---|---|---|
| Elemental analysis | C 43.43 | H 5.34 | C 45.82  H 4.91 |
| M.p. | not determinable, the substance foams from 140° C. | | similar to Example 1 |
| IR KBr | $1117 cm^{-1}$ 1275 1675 1755 | alcohol bands ester, COOH COOH, —C=O 5-ring lactone | similar to Example 1 |
| NMR | mixture, in part still the C-skeleton as in ascorbic acid | | similar to Example 1 |
| $H_2O$ solubility | about 25 g/100 ml (25° C.) | | about 25 g/100 ml (25° C.) |

Example 5

700 mg of potassium nitrate and 300 mg of the degradation product according to Example 1 are dissolved in 10 ml of water and evaporated to dryness under reduced pressure at 40° C. There is obtained 1 g of an explosive material with a heat of explosion (in the case of ignition with the exclusion of air) of 669 cal/g.

Example 6

When the procedure described in Example 5 is repeated using the product in accordance with Example 2 as the degradation product, there is obtained an explosive material with a heat of explosion of 700 cal/g.

We claim:

1. A process for producing an explosive composition comprising the steps of:
   a. heating ascorbic acid or isoascorbic acid in the absence of a nitrate containing substance at a temperature between about 70° C. and about 210° C. until about 10 to about 100 percent of the acid is degraded, forming a degradation product; and then
   b. at a temperature of less than about 40° C. mixing a nitrate-containing oxidization agent with said degradation product to form the explosive composition.

2. A process according to claim 1, wherein an alkali or alkaline earth nitrate or ammonium nitrate, or a mixture of these nitrates, is used as the nitrate-containing oxidation agent.

3. A process according to claim 2, wherein the weight ratio of the nitrate-containing oxidation agent to the degradation product is between 90:10 and 50:50, based on potassium nitrate as the oxidation agent.

4. A process according to claim 3, wherein the weight ratio of the nitrate-containing oxidation agent to the degradation product is between 80:20 and 60:40, based on potassium nitrate as the oxidation agent.

* * * * *